United States Patent
Takahashi et al.

(10) Patent No.: US 12,428,496 B2
(45) Date of Patent: Sep. 30, 2025

(54) ANTIBODIES, COMPOSITIONS FOR USE IN DETECTING OR CAPTURING A POLYPEPTIDE IN A SAMPLE, AND METHODS FOR DETECTING OR CAPTURING A POLYPEPTIDE IN A SAMPLE

(71) Applicant: Chugai Seiyaku Kabushiki Kaisha, Tokyo (JP)

(72) Inventors: Noriyuki Takahashi, Shizuoka (JP); Tomoyuki Igawa, Shizuoka (JP); Takeshi Baba, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 439 days.

(21) Appl. No.: 16/769,743

(22) PCT Filed: Dec. 7, 2018

(86) PCT No.: PCT/JP2018/045024
§ 371 (c)(1),
(2) Date: Jun. 4, 2020

(87) PCT Pub. No.: WO2019/112027
PCT Pub. Date: Jun. 13, 2019

(65) Prior Publication Data
US 2020/0369784 A1 Nov. 26, 2020

(30) Foreign Application Priority Data
Dec. 7, 2017 (JP) .................................. 2017-235244

(51) Int. Cl.
*C07K 16/00* (2006.01)
*C07K 16/42* (2006.01)
*G01N 33/53* (2006.01)
*G01N 33/68* (2006.01)

(52) U.S. Cl.
CPC ..... *C07K 16/4283* (2013.01); *G01N 33/6854* (2013.01); *C07K 2317/56* (2013.01)

(58) Field of Classification Search
None
See application file for complete search history.

(56) References Cited

U.S. PATENT DOCUMENTS

| 9,096,651 | B2 | 8/2015 | Igawa et al. | |
| 2011/0076275 | A1 | 3/2011 | Igawa et al. | |
| 2015/0210763 | A1 | 7/2015 | Kuramochi et al. | |
| 2020/0317790 | A1* | 10/2020 | Okura ................ | C07K 16/2833 |

FOREIGN PATENT DOCUMENTS

| EP | 2206775 A1 | 7/2010 |
| WO | WO 2009023457 A1 | 2/2009 |
| WO | WO 2009041613 A1 | 4/2009 |
| WO | WO 2014078475 A2 | 5/2014 |
| WO | WO 2017072210 A1 | 5/2017 |

OTHER PUBLICATIONS

Fukuzawa, T., et al., "Long lasting neutralization of C5 by SKY59, a novel recycling antibody, is a potential therapy for complement-mediated diseases," Scientific Reports, 7:1080 (2017).
Saito, T., et al., "Dosage Optimization of Nemolizumab Using Population Pharmacokinetic and Pharmacokinetic-Pharmacodynamic Modeling and Simulation," J Clin Pharmacol., 57(12):1564-1572 (2017).
Shima, M., et al., "Long-term safety and efficacy of emicizumab in a phase 1/2 study in patients with hemophilia A with or without inhibitors," Blood Adv., 1(22):1891-1899 (2017).
International Search Report dated Feb. 26, 2019 in International Application No. PCT/JP2018/045024.
Johnson, K. A., et al., "Cation exchange-HPLC and mass spectrometry reveal C-terminal amidation of an IgG1 heavy chain," Anal Biochem., 360:75-83 (2007).
Köhler, G. and Milstein, C., "Continuous cultures of fused cells secreting antibody of predefined specificity," 256:495-497 (1975).
Lagassé, H. A. D., et al., Recent advances in (therapeutic protein) drug development [version 1; peer review: 2 approved], F1000Research 2017, 6(F1000 Faculty Rev): 113, 17 pages.
Liu, H., et al., "Heterogeneity of Monoclonal Antibodies," J Pharm Sci., 97:2426-2447 (2008).
Mimoto, F., et al., "Fc Engineering to Improve the Function of Therapeutic Antibodies," Curr Pharm Biotechnol., 17:1298-1314 (2016).
Reichert, J. M., "Monoclonal Antibodies as Innovative Therapeutics," Curr Pharm Biotechnol., 9:423-430 (2008).
Yu, X-Q., et al., "Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults," Antimicrob Agents Chemother., 61(1):e01020-16 (2016).
U.S. Appl. No. 12/679,922, 371(c) date Oct. 1, 2010, Igawa, T. et al.
Japanese Patent Application No. 2017-193341 filed Oct. 3, 2017.
Japanese Patent Application No. 2017-235244 filed Dec. 7, 2017.

* cited by examiner

Primary Examiner — Kimberly Ballard
Assistant Examiner — Aditi Dutt
(74) Attorney, Agent, or Firm — Nixon & Vanderhye P.C.

(57) ABSTRACT

An objective of the invention is to provide an antibody, a composition for use in detecting or capturing a polypeptide in a sample, and a method for detecting or capturing a polypeptide in sample. The disclosure provides an antibody, a composition for use in detecting or capturing a polypeptide in a sample, and a method for detecting or capturing a polypeptide in sample.

26 Claims, 3 Drawing Sheets
Specification includes a Sequence Listing.

ANTIBODIES, COMPOSITIONS FOR USE IN DETECTING OR CAPTURING A POLYPEPTIDE IN A SAMPLE, AND METHODS FOR DETECTING OR CAPTURING A POLYPEPTIDE IN A SAMPLE

CROSS-REFERENCE TO RELATED APPLICATIONS

This application is a U.S. National Phase of PCT Application No. PCT/JP2018/045024, filed Dec. 7, 2018, which claims the benefit of Japanese Patent Application No. 2017-235244, filed Dec. 7, 2017, each of which is incorporated herein by reference in its entirety.

REFERENCE TO SEQUENCE LISTING SUBMITTED ELECTRONICALLY

The content of the electronically submitted sequence listing (Name: 6663 0135 Sequence_Listing.txt; Size: 7.09 kilobytes; and Date of Creation: Jun. 3, 2020) filed with the application is incorporated herein by reference in its entirety.

TECHNICAL FIELD

The present invention relates to antibodies, compositions for use in detecting or capturing a polypeptide in a sample, and methods for detecting or capturing a polypeptide in a sample.

BACKGROUND ART

Hybridoma technology has enabled the production of monoclonal antibodies and this monoclonal antibody technology has a wide range of applications in many scientific fields (NPL1). After this technological achievement, further efforts were made in the field of therapeutic and diagnostic antibodies. 30 years have passed since the first US approval of monoclonal antibody therapy (NPL2). More than 30 antibodies have been approved by the FDA and a significant number of candidates are under clinical and pre-clinical evaluation. So far, monoclonal antibodies have remained the standard therapeutic molecules and are used in various disease areas such as cancer, autoimmune diseases, respiratory diseases, infectious diseases and neural diseases (NPL3).

In order to increase the merit of therapeutic antibodies, many different types of engineered Fc modifications to improve functions such as those for antibody-dependent cell-mediated cytotoxicity enhancement, complement dependent cytotoxicity enhancement, antibody half-life extension, antigen clearance modulation and facilitation of heavy chain heterodimerization, were identified (NPL4).

During the process of therapeutic monoclonal antibody production, the heterogeneity of antibody molecules can cause potential difficulties in achieving consistent manufacturing and quality control (NPL5). Heavy chain C-terminal heterogeneity for recombinant monoclonal antibodies, comprising wild type heavy chain, C-terminus lysine-deleted heavy chain (referred to as "delta-K"), and heavy chain ending with amidated proline (referred to as "delta-GK-amide"), is one such example previously reported (NPL6). Interestingly, this cleaving event is similar to the modification of endogenous antibody Fc. In general, endogenous antibody heavy chain C-terminal lysine is cleaved by endogenous carboxypeptidase in vivo. Further modifications of C-terminal glycine cleavage and proline amidation have also been reported. This is because peptidylglycine alpha-amidating monooxygenase (PAM) cleaves C-terminal glycine and amidates proline.

To overcome this C-terminal heterogeneity problem, scientists have successfully identified the pivotal residues and engineered an antibody Fc whereby the C-terminal lysine (K) (position 447 in the EU numbering system) and glycine (G) (position 446 in the EU numbering system) are genetically deleted from the Fc region (referred to as "delta-GK") (PTL1).

Antibodies that specifically bind to engineered Fc regions but not to a wild-type Fc have been reported (NPL7; PTL2). It was proven that antibodies against engineered Fc regions are quite useful for various purposes.

CITATION LIST

Patent Literature

[PTL1] WO2009041613A1
[PTL2] WO2017072210A1

Non Patent Literature

[NPL1] Kohler, G. et al., Nature 256:495-497 (1975)
[NPL2] Reichert, J. M. et al., Curr. Pharm. Biotechnol. 9:423-430 (2008)
[NPL3] Lagasse HAD et al. F1000Research 2017, 6 (F1000 Faculty Rev):113
[NPL4] Mimoto et al., Curr. Pharm. Biotechnol. 17:1298-1314 (2016)
[NPL5] Liu, H. et al., J. Pharm. Sci. 97: 2426-2447 (2008)
[NPL6] K. A. Johnson et al., Anal. Biochem. 360:75-83 (2007)
[NPL7] Yu et al., Antimicrob Agents Chemother. 61 (2016)

SUMMARY OF INVENTION

We have provided some antibodies comprising a modified IgG heavy chain constant region which has originated from a human IgG heavy chain constant region and lacks both of glycine at position 446 according to the EU numbering system and lysine at position 447 according to the EU numbering system, and in which an amino acid at position 445 according to the EU numbering system remains, the set of modifications in such modified IgG heavy chain constant region being referred to as "IgG delta-GK" herein and antibodies comprising a modified IgG heavy chain constant region having the IgG delta-GK include, for example, satralizumab, nemolizumab, emicizumab, SKY59, AMY109, and GYM329. The present invention provides antibodies that specifically bind to, detect, and capture such delta-GK in a modified IgG heavy chain constant region, compositions comprising the antibody, and methods using the antibody.

Specifically, the present invention relates to:

[1] An antibody that specifically binds to a first modified IgG heavy chain constant region which has originated from human IgG heavy chain constant region, wherein the first modified IgG heavy chain constant region lacks both of glycine at position 446 according to the EU numbering system and lysine at position 447 according to the EU numbering system, wherein an amino acid at position 445 according to the EU numbering system remains in the first modified IgG heavy chain constant region.

[2] The antibody of [1], wherein the amino acid at position 445 according to the EU numbering system in the first modified IgG heavy chain constant region is not amidated.

[3] The antibody of [2], which substantially does not bind to a second modified IgG heavy chain constant region which has originated from human IgG heavy chain constant region, wherein the second modified IgG heavy chain constant region lacks both of glycine at position 446 according to the EU numbering system and lysine at position 447 according to the EU numbering system, wherein an amino acid at position 445 according to the EU numbering system remains in the second modified IgG heavy chain constant region and is amidated.

[4] The antibody of any one of [1] to [3], which substantially does not bind to the following (i) or (ii):
  (i) a third modified IgG heavy chain constant region which has originated from human IgG heavy chain constant region or a non-modified human IgG heavy chain constant region, wherein an amino acids at position 445, position 446, and position 447 according to the EU numbering system remain in the third modified IgG heavy chain constant region or the non-modified human IgG heavy chain constant region; and
  (ii) a fourth modified IgG heavy chain constant region which has originated from human IgG heavy chain constant region, wherein the fourth modified IgG heavy chain constant region lacks lysine at position 447 according to the EU numbering system, wherein an amino acids at position 445 and position 446 according to the EU numbering system remain in the fourth modified IgG heavy chain constant region.

[5] The antibody of [3], wherein a binding activity of the antibody to the second modified IgG heavy chain constant region is below the detection limit in an enzyme-linked immunoassay.

[6] The antibody of [4], wherein a binding activity of the antibody to at least one IgG heavy chain constant region selected from the group consisting of the third modified IgG heavy chain constant region, the fourth modified IgG heavy chain constant region, and the non-modified human IgG heavy chain constant region is below the detection limit in an enzyme-linked immunoassay.

[7] The antibody of any one of [1] to [6], wherein a binding activity of the antibody to the first modified IgG heavy chain constant region is detectable in an enzyme-linked immunoassay.

[8] The antibody of any one of [1] to [7], wherein the antibody competes for binding to the first modified IgG heavy chain constant region with an antibody which comprises:
  (a) HVR-H1 comprising the amino acid sequence of SEQ ID NO: 2;
  (b) HVR-H2 comprising the amino acid sequence of SEQ ID NO: 3;
  (c) HVR-H3 comprising the amino acid sequence of SEQ ID NO: 4;
  (d) HVR-L1 comprising the amino acid sequence of SEQ ID NO: 6;
  (e) HVR-L2 comprising the amino acid sequence of SEQ ID NO: 7; and
  (f) HVR-L3 comprising the amino acid sequence of SEQ ID NO: 8.

[9] The antibody of any one of [1] to [8], wherein the antibody binds to the same epitope as an antibody which comprises:
  (a) HVR-H1 comprising the amino acid sequence of SEQ ID NO: 2;
  (b) HVR-H2 comprising the amino acid sequence of SEQ ID NO: 3;
  (c) HVR-H3 comprising the amino acid sequence of SEQ ID NO: 4;
  (d) HVR-L1 comprising the amino acid sequence of SEQ ID NO: 6;
  (e) HVR-L2 comprising the amino acid sequence of SEQ ID NO: 7; and
  (f) HVR-L3 comprising the amino acid sequence of SEQ ID NO: 8.

[10] A composition for use in detecting or capturing a polypeptide in a sample, wherein the composition comprises the antibody of any one of [1] to [9], and the polypeptide comprises a fifth modified IgG heavy chain constant region which has originated from human IgG heavy chain constant region, wherein the fifth modified IgG heavy chain constant region lacks both of glycine at position 446 according to the EU numbering system and lysine at position 447 according to the EU numbering system, wherein an amino acid at position 445 according to the EU numbering system remains in the fifth modified IgG heavy chain constant region.

[11] The composition of [10], wherein the amino acid at position 445 according to the EU numbering system in the fifth modified IgG heavy chain constant region is not amidated.

[12] A method for detecting or capturing a polypeptide in a sample, wherein the method comprises contacting the antibody of any one of [1] to [8] with the sample, and the polypeptide comprises a sixth modified IgG heavy chain constant region which has originated from human IgG heavy chain constant region, wherein the sixth modified IgG heavy chain constant region lacks both of glycine at position 446 according to the EU numbering system and lysine at position 447 according to the EU numbering system, wherein an amino acid at position 445 according to the EU numbering system remains in the sixth modified IgG heavy chain constant region.

[13] The method of [12], wherein the amino acid at position 445 according to the EU numbering system in the sixth modified IgG heavy chain constant region is not amidated.

DESCRIPTION OF EMBODIMENTS

I. Definition

Figure 1:
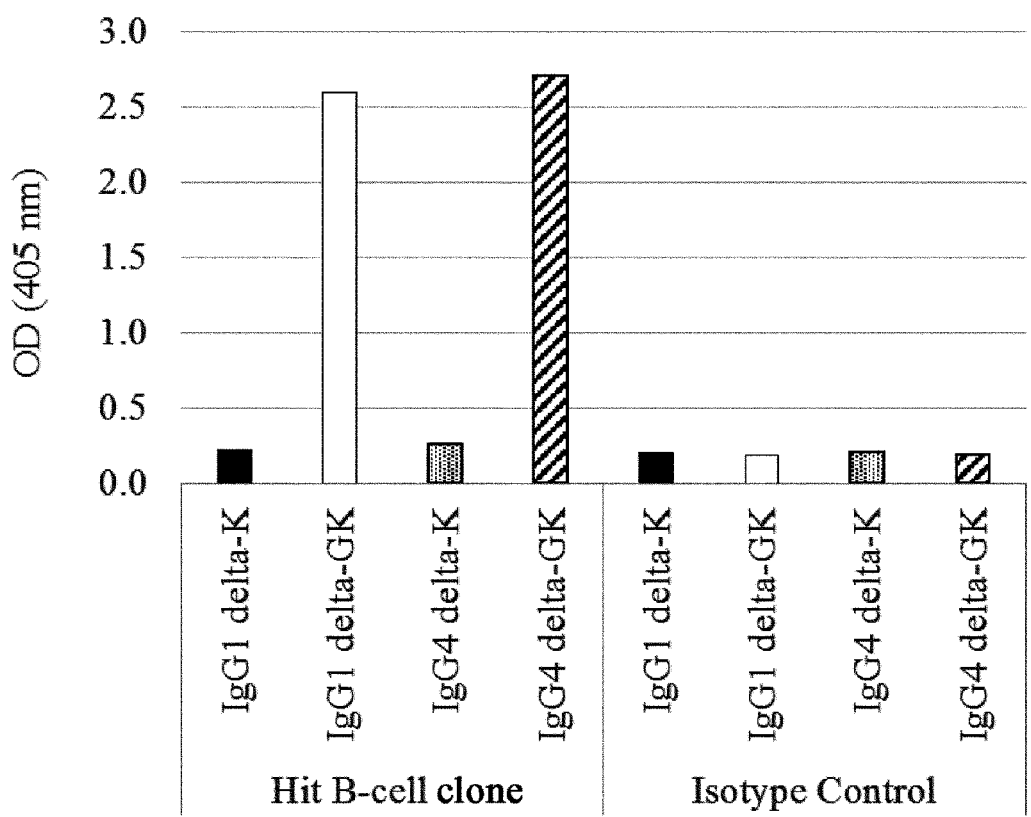
FIG. 1 shows the ELISA results of the primary screening. The identified single hit (positive) B-cell clone could bind to IgG1 delta-GK and IgG4 delta-GK specifically, and did not bind to IgG1 delta-K and IgG4 delta-K. An anti-keyhole limpet hemocyanin (KLH) rabbit monoclonal antibody was used as an isotype control.

"Affinity" refers to the strength of the sum total of noncovalent interactions between a single binding site of a molecule (e.g., an antibody) and its binding partner (e.g., an antigen). Unless indicated otherwise, as used herein, "binding affinity" or "binding activity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described below.

The term "an antibody that specifically binds to a modified IgG heavy chain constant region which has originated from a human IgG heavy chain constant region" refers to an antibody that is capable of binding to a specific type of modified IgG heavy chain constant region with sufficient affinity such that the antibody is useful as a detection, capturing, or diagnostic agent in targeting the modified IgG heavy chain constant region. In one embodiment, for an antibody that specifically binds to a first modified IgG heavy chain constant region which has originated from a human IgG heavy chain constant region, the extent of binding of the antibody, which specifically binds to the first modified IgG heavy chain constant region, to an IgG heavy chain constant region(s) other than the first modified IgG heavy chain constant region, e.g., second, third, and fourth modified IgG heavy chain constant regions and a non-modified human IgG heavy chain constant region, is less than about 10% of the binding of the first modified IgG heavy chain constant region as measured, e.g., by a radioimmunoassay (RIA). In certain embodiments, an antibody that binds to a modified IgG heavy chain constant region which has originated from a human IgG heavy chain constant region has a dissociation constant (Kd) of 1 micro M or less, 100 nM or less, 10 nM or less, 1 nM or less, 0.1 nM or less, 0.01 nM or less, or 0.001 nM or less (e.g., $10^{-8}$M or less, e.g. from $10^{-8}$M to $10^{-13}$M, e.g., from $10^{-9}$M to $10^{-13}$ M). In certain embodiments, an antibody that binds to a modified IgG heavy chain constant region which has originated from a human IgG heavy chain constant region binds to an epitope of the modified IgG heavy chain constant region.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

II. Antibody

An antibody in the present invention specifically binds to a first modified IgG heavy chain constant region which has originated from human IgG heavy chain constant region. The first modified IgG heavy chain constant region lacks both of glycine at position 446 according to the EU numbering system and lysine at position 447 according to the EU numbering system. An amino acid at position 445 according to the EU numbering system remains in the first modified IgG heavy chain constant region.

In a further aspect of the invention, the antibody that specifically binds to the first modified IgG heavy chain constant region which has originated from human IgG heavy chain constant region is a monoclonal antibody, including a chimeric, humanized or human antibody. In one embodiment, the antibody is an antibody fragment, e.g., a Fv, Fab, Fab', scFv, diabody, or F(ab')2 fragment. In another embodiment, the antibody is a full length antibody, e.g., an intact IgG1, IgG2, IgG3 and IgG4 antibodies, or other antibody class or isotype as defined herein.

A. A First Modified IgG Heavy Chain Constant Region

In one embodiment, a first modified IgG heavy chain constant region may form a dimer, such as a heavy chain constant region in a naturally occurring IgG, or may form a halfmer, such as a heavy chain constant region in the monomeric Fc reported in Ishino, T. et al., J. Biol. Chem. 288:16529-37 (2013).

In one embodiment, a first modified IgG heavy chain constant region may have originated from a part of a human IgG heavy chain constant region. In a preferred embodiment, the first modified IgG heavy chain constant region comprises at least a region corresponding to a CH3 region of a human IgG heavy chain. In this embodiment, an epitope to which the antibody binds may be positioned in the range of said at least a region corresponding to a CH3 region of a human IgG heavy chain. In a further preferred embodiment, the first modified IgG heavy chain constant region comprises at least regions corresponding to a CH2 region and a CH3 region of a human IgG heavy chain. In this embodiment, an epitope to which the antibody binds may be positioned in the range of said at least regions corresponding to a CH2 region and a CH3 region of a human IgG heavy chain. In a still more preferred embodiment, the first modified IgG heavy chain constant region comprises at least a region corresponding to an Fc region of a human IgG heavy chain. In this embodiment, an epitope to which the antibody binds may be positioned in the range of said at least a region corresponding to an Fc region of a human IgG heavy chain.

In one embodiment, when a first modified IgG heavy chain constant region is in a human modified IgG heavy chain, the human modified IgG heavy chain is selected from the group consisting of human IgG1, IgG2, IgG3 and IgG4 heavy chains. In a preferred embodiment, the human IgG heavy chain is a human IgG1 or IgG4 heavy chain.

In a preferred embodiment, the amino acid at position 445 according to the EU numbering system in the first modified IgG heavy chain constant region is not amidated.

A set of modifications in a modified IgG heavy chain constant region, i.e., lacking both of glycine at position 446 according to the EU numbering system and lysine at position 447 according to the EU numbering system while retaining a non-amidated amino acid at position 445 according to the EU numbering system, such as the one in a preferred first modified IgG heavy chain constant region, is called "IgG delta-GK" or "delta-GK" herein.

In a further preferred embodiment, the antibody substantially does not bind to an IgG heavy chain constant region comprising delta-GK-amide, which is a second modified IgG heavy chain constant region which has originated from a human IgG heavy chain constant region. The second modified IgG heavy chain constant region lacks both of glycine at position 446 according to the EU numbering system and lysine at position 447 according to the EU numbering system. An amino acid at position 445 according to the EU numbering system remains in the second modified IgG heavy chain constant region and is amidated.

In all of that, the antibody can distinguish the modified IgG heavy chain constant region with the non-amidated amino acid at position 445 according to the EU numbering system in a human modified IgG heavy chain constant region, from the modified IgG heavy chain constant region with delta-GK-amide.

In one embodiment, a binding activity of the antibody to the second modified IgG heavy chain constant region is below the detection limit in an enzyme-linked immunoassay.

In another embodiment, a binding activity of the antibody to the first modified IgG heavy chain constant region is detectable in an enzyme-linked immunoassay.

B. Human IgG Heavy Chain Constant Regions to which the Antibody Substantially does not Bind In one embodiment, the antibody substantially does not bind to (i) a third modified IgG heavy chain constant region with "not-deleted C-terminus", which has originated from a human IgG heavy chain constant region, or a non-modified human IgG heavy chain constant region, or (ii) a fourth modified IgG heavy chain constant region which has originated from a human IgG heavy chain constant region, comprising "delta-K".

In the third modified IgG heavy chain constant region comprising not-deleted C-terminus or the non-modified human IgG heavy chain constant region of (i), amino acids at position 445, position 446, and position 447 according to the EU numbering system remain.

The fourth modified IgG heavy chain constant region with delta-K in (ii) lacks lysine at position 447 according to the EU numbering system. Amino acids at position 445 and position 446 according to the EU numbering system remain in the fourth modified IgG heavy chain constant region in (ii).

In all of that, the antibody can distinguish the first modified IgG heavy chain constant region from the modified IgG heavy chain constant region with not-deleted C-terminus or delta-K, or the non-modified human IgG heavy chain constant region.

In one embodiment, a binding activity of the antibody to at least one IgG heavy chain constant region selected from the group consisting of the third modified IgG heavy chain constant region, the fourth modified IgG heavy chain constant region, and the non-modified human IgG heavy chain constant region is below the detection limit in an enzyme-linked immunoassay.

C. YG55

Because an antibody binds to its antigen by its variable region, the variable region is important for binding specificity of the antibody. Furthermore, it is generally known that hypervariable regions (HVRs) are the most important region for binding specificity of the antibody.

The inventors obtained, by screening, the antibodies which are encompassed in the above-mentioned antibody as explained in "Examples", one of them is named "YG55", while the scope of the present invention is not limited to this particular antibody YG55. Based on the above-mentioned general knowledge, the inventors identified all HVRs of YG55. YG55 comprises (a) HVR-H1 comprising the amino acid sequence of SEQ ID NO: 2, (b) HVR-H2 comprising the amino acid sequence of SEQ ID NO: 3, (c) HVR-H3 comprising the amino acid sequence of SEQ ID NO: 4, (d) HVR-L1 comprising the amino acid sequence of SEQ ID NO: 6, (e) HVR-L2 comprising the amino acid sequence of SEQ ID NO: 7, and (0 HVR-L3 comprising the amino acid sequence of SEQ ID NO: 8.

In one aspect, the invention provides an antibody comprising at least one, two, three, four, five, or six HVRs selected from (a) HVR-H1 comprising the amino acid sequence of SEQ ID NO: 2; (b) HVR-H2 comprising the amino acid sequence of SEQ ID NO: 3; (c) HVR-H3 comprising the amino acid sequence of SEQ ID NO: 4; (d) HVR-L1 comprising the amino acid sequence of SEQ ID NO: 6; (e) HVR-L2 comprising the amino acid sequence of SEQ ID NO: 7; and (0 HVR-L3 comprising the amino acid sequence of SEQ ID NO: 8.

In one aspect, the invention provides an antibody comprising at least one, at least two, or all three VH HVR sequences selected from (a) HVR-H1 comprising the amino acid sequence of SEQ ID NO: 2; (b) HVR-H2 comprising the amino acid sequence of SEQ ID NO: 3; and (c) HVR-H3 comprising the amino acid sequence of SEQ ID NO: 4. In one embodiment, the antibody comprises HVR-H3 comprising the amino acid sequence of SEQ ID NO: 4. In another embodiment, the antibody comprises HVR-H3 comprising the amino acid sequence of SEQ ID NO: 4 and HVR-L3 comprising the amino acid sequence of SEQ ID NO: 8. In a further embodiment, the antibody comprises HVR-H3 comprising the amino acid sequence of SEQ ID NO: 4, HVR-L3 comprising the amino acid sequence of SEQ ID NO: 8, and HVR-H2 comprising the amino acid sequence of SEQ ID NO: 3. In a further embodiment, the antibody comprises (a) HVR-H1 comprising the amino acid sequence of SEQ ID NO: 2; (b) HVR-H2 comprising the amino acid sequence of SEQ ID NO: 3; and (c) HVR-H3 comprising the amino acid sequence of SEQ ID NO: 4.

In another aspect, the invention provides an antibody comprising at least one, at least two, or all three VL HVR sequences selected from (a) HVR-L1 comprising the amino acid sequence of SEQ ID NO: 6; (b) HVR-L2 comprising the amino acid sequence of SEQ ID NO: 7; and (c) HVR-L3 comprising the amino acid sequence of SEQ ID NO: 8. In one embodiment, the antibody comprises (a) HVR-L1 comprising the amino acid sequence of SEQ ID NO: 6; (b) HVR-L2 comprising the amino acid sequence of SEQ ID NO: 7; and (c) HVR-L3 comprising the amino acid sequence of SEQ ID NO: 8.

In another aspect, an antibody of the invention comprises (a) a VH domain comprising at least one, at least two, or all three VH HVR sequences selected from (i) HVR-H1 comprising the amino acid sequence of SEQ ID NO: 2, (ii) HVR-H2 comprising the amino acid sequence of SEQ ID NO: 3, and (iii) HVR-H3 comprising the amino acid sequence of SEQ ID NO: 4; and (b) a VL domain comprising at least one, at least two, or all three VL HVR sequences selected from (i) HVR-L1 comprising the amino acid sequence of SEQ ID NO: 6, (ii) HVR-L2 comprising the amino acid sequence of SEQ ID NO: 7, and (c) HVR-L3 comprising the amino acid sequence of SEQ ID NO: 8.

In another aspect, the invention provides an antibody comprising (a) HVR-H1 comprising the amino acid sequence of SEQ ID NO: 2; (b) HVR-H2 comprising the amino acid sequence of SEQ ID NO: 3; (c) HVR-H3 comprising the amino acid sequence of SEQ ID NO: 4; (d) HVR-L1 comprising the amino acid sequence of SEQ ID NO: 6; (e) HVR-L2 comprising the amino acid sequence of SEQ ID NO: 7; and (0 HVR-L3 comprising the amino acid sequence selected from SEQ ID NO: 8.

In another aspect, an antibody described herein comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 1. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody described herein comprising that sequence retains the ability to bind to a first modified IgG heavy chain constant region. In certain embodiments, a total of 1 to 10 amino acids have been substituted, inserted and/or deleted in SEQ ID NO: 1. In certain embodiments, substitutions, insertions, or deletions occur in regions outside the HVRs (i.e., in the FRs). Optionally, the antibody comprises the VH sequence in SEQ ID NO: 1, including post-translational modifications of that sequence. In a particular embodiment, the VH comprises one, two or three HVRs selected from: (a) HVR-H1 comprising the amino acid sequence of SEQ ID NO: 2, (b) HVR-H2 comprising the amino acid sequence of SEQ ID NO: 3, and (c) HVR-H3 comprising the amino acid sequence of SEQ ID NO: 4. Post-translational modifications include but are not limited to a modification of glutamine or glutamate in N-terminal of heavy chain or light chain to pyroglutamic acid by pyroglutamylation.

In another aspect, an antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 5. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody comprising that sequence retains the ability to bind to a first modified IgG heavy chain constant region. In certain embodiments, a total of 1 to 10 amino acids have been substituted, inserted and/or deleted in SEQ ID NO: 5. In certain embodiments, the substitutions, insertions, or deletions occur in regions outside the HVRs (i.e., in the FRs). Optionally, the antibody comprises the VL sequence in SEQ ID NO: 5, including post-translational modifications of that sequence. In a particular embodiment, the VL comprises one, two or three HVRs selected from (a) HVR-L1 comprising the amino acid sequence of SEQ ID NO: 6; (b) HVR-L2 comprising the amino acid sequence of SEQ ID NO: 7; and (c) HVR-L3 comprising the amino acid sequence of SEQ ID NO: 8. Post-translational modifications include but are not limited to a modification of glutamine or glutamate in N-terminal of heavy chain or light chain to pyroglutamic acid by pyroglutamylation.

In another aspect, an antibody is provided, wherein the antibody comprises a VH as in any of the embodiments provided above, and a VL as in any of the embodiments provided above. In one embodiment, the antibody comprises the VH and VL sequences in SEQ ID NO: 1 and SEQ ID NO: 5, respectively, including post-translational modifications of those sequences. Post-translational modifications include but are not limited to a modification of glutamine or glutamate in N-terminal of heavy chain or light chain to pyroglutamic acid by pyroglutamylation.

In one aspect, an antibody is provided, wherein the antibody competes for binding to the first modified IgG heavy chain constant region with an antibody which comprises:
(a) HVR-H1 comprising the amino acid sequence of SEQ ID NO: 2;
(b) HVR-H2 comprising the amino acid sequence of SEQ ID NO: 3;
(c) HVR-H3 comprising the amino acid sequence of SEQ ID NO: 4;
(d) HVR-L1 comprising the amino acid sequence of SEQ ID NO: 6;
(e) HVR-L2 comprising the amino acid sequence of SEQ ID NO: 7; and
(f) HVR-L3 comprising the amino acid sequence of SEQ ID NO: 8.

In one aspect, an antibody is provided, wherein the antibody binds to the same epitope as an antibody which comprises:
(a) HVR-H1 comprising the amino acid sequence of SEQ ID NO: 2;
(b) HVR-H2 comprising the amino acid sequence of SEQ ID NO: 3;
(c) HVR-H3 comprising the amino acid sequence of SEQ ID NO: 4;
(d) HVR-L1 comprising the amino acid sequence of SEQ ID NO: 6;
(e) HVR-L2 comprising the amino acid sequence of SEQ ID NO: 7; and
(f) HVR-L3 comprising the amino acid sequence of SEQ ID NO: 8.

D. Recombinant Methods and Compositions

Antibodies may be produced using recombinant methods and compositions, e.g., as described in U.S. Pat. No. 4,816,567. In one embodiment, isolated nucleic acid(s) encoding an antibody described herein is provided. Such nucleic acids may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acids are provided. In a further embodiment, a host cell comprising such nucleic acids is provided. In one such embodiment, a host cell comprises (e.g., has been transformed with): (1) a vector comprising a nucleic acid molecule that encodes an amino acid sequence comprising the VL of the antibody and an amino acid sequence comprising the VH of the antibody, or (2) a first vector comprising a nucleic acid molecule that encodes an amino acid sequence comprising the VL of the antibody and a second vector comprising a nucleic acid molecule that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp2/0 cell). In one embodiment, a method of making an antibody described herein is provided, wherein the method comprises culturing a host cell comprising a nucleic acid molecule encoding the antibody, as provided above, under conditions suitable for expression of the antibody, and optionally recovering the antibody from the host cell (or host cell culture medium).

For recombinant production of an antibody described herein, a nucleic acid molecule encoding an antibody, e.g., as described above, is isolated and inserted into one or more vectors for further cloning and/or expression in a host cell. Such nucleic acid molecule may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as YO, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

E. Assays

Antibodies provided herein may be identified, screened for, or characterized for their physical/chemical properties and/or biological activities by various assays known in the art.

F. Binding Assays and Other Assays

In one aspect, an antibody of the invention is tested for its antigen binding activity, e.g., by known methods such as ELISA, Western blot, etc.

In another aspect, competition assays may be used to identify an antibody that competes with YG55 used in "Examples" for binding to a first modified IgG heavy chain constant region. In certain embodiments, such a competing antibody binds to the same epitope (e.g., a linear or a conformational epitope) that is bound by YG55 used in "Examples". Detailed exemplary methods for mapping an epitope to which an antibody binds are provided in Morris (1996) "Epitope Mapping Protocols," in Methods in Molecular Biology vol. 66 (Humana Press, Totowa, NJ).

In an exemplary competition assay, immobilized first modified IgG heavy chain constant region is incubated in a solution comprising a first labeled antibody that binds to the first modified IgG heavy chain constant region and a second unlabeled antibody that is being tested for its ability to compete with the first antibody for binding to the first modified IgG heavy chain constant region. The second antibody may be present in a B-cell or hybridoma supernatant. As a control, immobilized first modified IgG heavy chain constant region is incubated in a solution comprising the first labeled antibody but not the second unlabeled antibody. After incubation under conditions permissive for binding of the first antibody to the first modified IgG heavy chain constant region, excess unbound antibody is removed, and the amount of label associated with immobilized IgG heavy chain constant region is measured. If the amount of label associated with immobilized IgG heavy chain constant region is substantially reduced in the test sample relative to the control sample, then that indicates that the second antibody is competing with the first antibody for binding to the first modified IgG heavy chain constant region. See Harlow and Lane (1988) Antibodies: A Laboratory Manual ch. 14 (Cold Spring Harbor Laboratory, Cold Spring Harbor, NY).

III. Composition

In one aspect, a composition in the present invention is a composition for use in detecting or capturing a polypeptide in a sample. The composition comprises the antibody mentioned in "II. Antibody". The polypeptide comprises a fifth modified IgG heavy chain constant region which has originated from a human IgG heavy chain constant region. The fifth modified IgG heavy chain constant region lacks both of glycine at position 446 according to the EU numbering system and lysine at position 447 according to the EU numbering system and an amino acid at position 445 according to the EU numbering system remains in the fifth modified IgG heavy chain constant region.

In a preferred embodiment, the amino acid at position 445 according to the EU numbering system in the fifth modified IgG heavy chain constant region is not amidated.

The fifth modified IgG heavy chain constant region may comprise other amino acid substitutions or modifications as long as it comprises the modifications of lacking both of glycine at position 446 according to the EU numbering system and lysine at position 447 according to the EU numbering system and retaining an amino acid at position 445 according to the EU numbering system.

Furthermore, the polypeptide detected or captured using the composition in the present invention is not particularly limited in terms of its structure as long as the polypeptide comprises the fifth modified IgG heavy chain constant region at the C terminus. The polypeptide detected or captured using the composition in the present invention may be an antibody such as a human IgG1, IgG2, IgG3, or IgG4 molecule, an antibody fragment, a fusion protein, or a polypeptide of any other form comprising the fifth modified IgG heavy chain constant region.

IV. Method

In one aspect, a method in the present invention is a method for detecting or capturing a polypeptide in a sample. The method comprises contacting the antibody mentioned in "II. Antibody" with the sample. The polypeptide comprises a sixth modified IgG heavy chain constant region which has originated from human IgG heavy chain constant region. The sixth modified IgG heavy chain constant region lacks both of glycine at position 446 according to the EU numbering system and lysine at position 447 according to the EU numbering system and an amino acid at position 445 according to the EU numbering system remains in the sixth modified IgG heavy chain constant region.

In a preferred embodiment, the amino acid at position 445 according to the EU numbering system in the sixth modified IgG heavy chain constant region is not amidated.

The sixth modified IgG heavy chain constant region may comprise other amino acid substitutions or modifications as long as it comprises the modifications of lacking both of glycine at position 446 according to the EU numbering system and lysine at position 447 according to the EU numbering system and retaining an amino acid at position 445 according to the EU numbering system.

Furthermore, the polypeptide detected or captured by the method in the present invention is not particularly limited in terms of its structure as long as the polypeptide comprises the sixth modified IgG heavy chain constant region at the C terminus. The polypeptide detected or captured by the method in the present invention may be an antibody such as a human IgG1, IgG2, IgG3, or IgG4 molecule, an antibody fragment, a fusion protein, or a polypeptide of any other form comprising the sixth modified IgG heavy chain constant region.

EXAMPLES

Example 1

Preparation of Delta-GK Fc

The human IgG4-derived delta-GK Fc fragment was expressed using the FreeStyle™ 293 expression system (Invitrogen). The expressed Fc fragment was purified from the harvested cell culture media by affinity chromatography (MabSelect SuRe, GE). In the final step, the buffer was exchanged to D-PBS(–).

Example 2

Generation of Anti-Delta-GK Antibodies

Anti-delta-GK antibodies were prepared, selected, and assayed as described below.

NZW rabbits were immunized intradermally with the human IgG4-derived delta-GK Fc fragment expressed in Example 1 (100-200 micro g/dose/head). The dose was repeatedly given 6 times over a 3-month period followed by blood and spleen collection. For B-cell selection, an IgG4 delta-GK antibody (an IgG4 antibody with genetically deleted IgG4 C-terminal GK) and a wild type IgG4 antibody were prepared. Delta-GK specific B-cells were sorted using a cell sorter and then plated and cultured according to the procedure described in WO2016098356A1. After cultivation, the B-cell culture supernatants were harvested for further analysis and the corresponding B-cell pellets were cryopreserved.

Specific binding to IgG delta-GK was evaluated by ELISA using the B-cell culture supernatants. In this primary screening, four types of antibodies were used as antigens in order to evaluate the binding specificity against the delta-GK C-terminal sequence: an IgG1 antibody with genetically deleted IgG1 C-terminal K (IgG1 delta-K), an IgG1 antibody with genetically deleted IgG1 C-terminal GK (IgG1 delta-GK), an IgG4 antibody with genetically deleted IgG4 C-terminal K (IgG4 delta-K) and an IgG4 antibody with genetically deleted IgG4 C-terminal GK (IgG4 delta-GK). The results showed that only one culture supernatant sample from a single B cell clone demonstrated specific binding to both IgG1 delta-GK and IgG4 delta-GK (FIG. 1).

Figure 2:
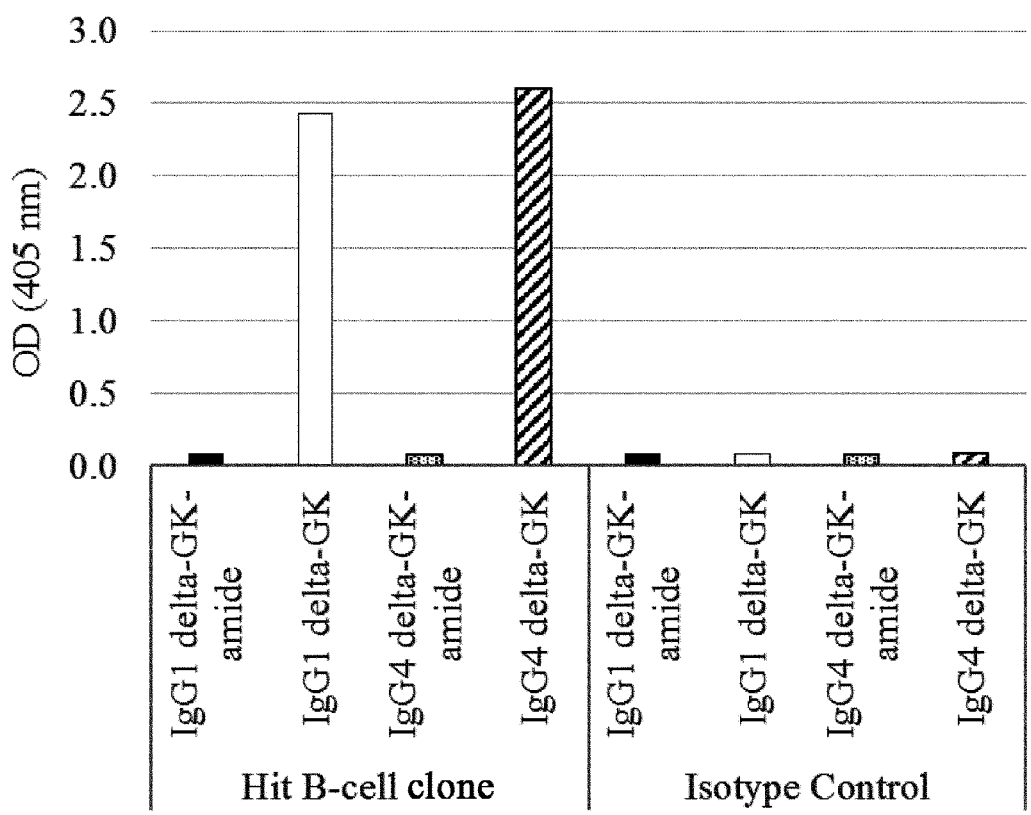
FIG. 2 shows the ELISA results of the secondary screening. The identified single hit (positive) B-cell clone could bind to IgG1 delta-GK and IgG4 delta-GK specifically, and did not bind to IgG1 delta-GK-amide and IgG4 delta-GK-amide. An anti-KLH rabbit monoclonal antibody was used as an isotype control.

Delta-GK Fc is more structurally similar to delta-GK-amide Fc than to delta-K Fc. We have also characterized specific binding to delta-GK Fc and delta-GK-amide Fc using the aforementioned selected culture supernatant from the positive B cell clone. IgG1 delta-GK-amide and IgG4 delta-GK-amide were prepared by PAM treatment with IgG1 delta-K or IgG4 delta-K mentioned above and were purified by conventional method. In this secondary screening, four types of antibodies were used as antigens in an ELISA assay to evaluate the binding specificity against the delta-GK C-terminal sequence: IgG1 delta-GK, IgG1 delta-GK-amide, IgG4 delta-GK, and IgG4 delta-GK-amide. Surprisingly, the tested single B cell culture supernatant showed extremely high specificity against delta-GK molecules (FIG. 2).

Based on these screening results, the RNA of the selected clone was extracted from its cryopreserved cell pellet using ZR-96 Quick-RNA kits (ZYMO RESEARCH, Cat No. R1053). DNA encoding the antibody heavy chain variable region in the antibody produced by the selected clone was obtained and amplified by reverse transcription PCR then recombined with DNA encoding the rabbit IgG heavy chain constant region (SEQ ID NO: 9). DNA encoding the antibody light chain variable regions was also obtained and amplified by reverse transcription PCR then recombined with DNA encoding the rabbit Igk light chain constant region (SEQ ID NO: 10). An anti-delta-GK antibody, named "YG55", which has two heavy chains and two light chains, was produced from these recombinants. The VH, VL, and HVRs sequences of the heavy and light chains are described in Table 1. YG55 was expressed using the FreeStyle™ 293 expression system and purified from the culture supernatants.

Example 3

Characterization of Anti-Delta-GK Monoclonal Antibody YG55

Figure 3:
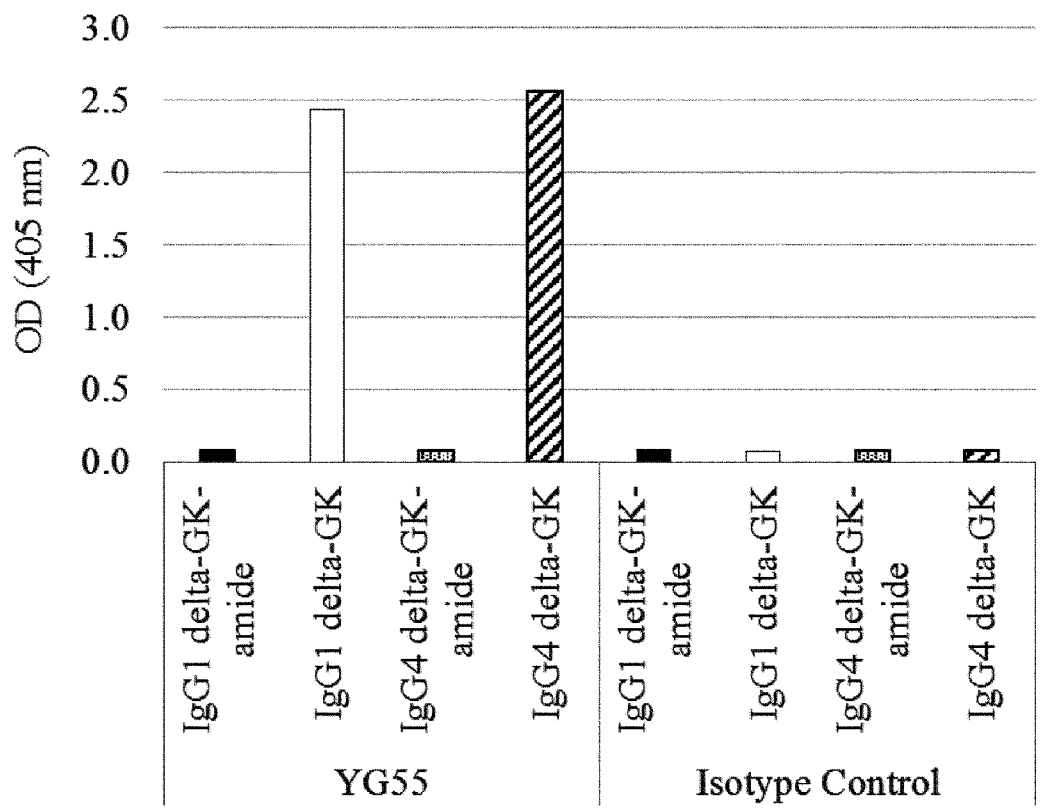
FIG. 3 shows the ELISA result of the purified monoclonal antibody. YG55 could bind to IgG1 delta-GK and IgG4 delta-GK specifically, and did not bind to IgG1 delta-GKamide and IgG4 delta-GK-amide. An anti-KLH rabbit monoclonal antibody was used as an isotype control.

After gene cloning and antibody expression, the specificity of YG55 was assessed by the ELISA assay as described above in the secondary screening. The antibody gene cloning was successful, resulting in YG55 retaining the same specificity shown by the hit (positive) B-cell clone (FIG. 3). This highly specific binding was also confirmed by surface plasmon resonance assay. The specific binding motif and its epitope were identified by crystal structure analysis.

TABLE 1

| Antibody Name | SEQ ID NO. | | | | | | | |
|---|---|---|---|---|---|---|---|---|
| | VH | HVR-H1 | HVR-H2 | HVR-H3 | VL | HVR-L1 | HVR-L2 | HVR-L3 |
| YG55 | 1 | 2 | 3 | 4 | 5 | 6 | 7 | 8 |

Sequence Listing C1-A1726P sequence txt

The invention claimed is:

1. An antibody which comprises:
   (a) HVR-H1 comprising the amino acid sequence of SEQ ID NO: 2;
   (b) HVR-H2 comprising the amino acid sequence of SEQ ID NO: 3;
   (c) HVR-H3 comprising the amino acid sequence of SEQ ID NO: 4;
   (d) HVR-L1 comprising the amino acid sequence of SEQ ID NO: 6;
   (e) HVR-L2 comprising the amino acid sequence of SEQ ID NO: 7; and
   (f) HVR-L3 comprising the amino acid sequence of SEQ ID NO: 8.

2. The antibody of claim 1, comprising:
   (a) a heavy chain variable domain comprising the amino acid sequence of SEQ ID NO: 1; and
   (b) a light chain variable domain comprising the amino acid sequence of SEQ ID NO: 5.

3. The antibody of claim 1, wherein the antibody is a monoclonal antibody.

4. The antibody of claim 1, wherein the antibody is a full-length antibody.

5. The antibody of claim 1, wherein the antibody is humanized.

6. The antibody of claim 1, wherein the antibody is an antigen binding fragment of an antibody.

7. The antibody of claim 6, wherein the antigen binding fragment of the antibody is a Fv, Fab, Fab', scFv, diabody, or a F(ab')2.

8. An antibody that specifically binds a modified IgG heavy chain constant region, wherein the antibody comprises:
   (a) a heavy chain variable domain comprising an amino acid sequence having 95% or higher sequence identity with the amino acid sequence of SEQ ID NO: 1; and
   (b) a light chain variable domain comprising an amino acid sequence having 95% or higher sequence identity with the amino acid sequence of SEQ ID NO: 5.

9. A method for detecting a polypeptide containing a modified IgG heavy chain constant region in a sample, wherein the method comprises contacting a sample containing a modified IgG heavy chain capable of being bound by the antibody of claim 1 with the antibody.

10. The method of claim 9, wherein detection of the polypeptide by binding the antibody is determined by ELISA or surface plasmon resonance.

11. The method of claim 9, wherein the antibody is a monoclonal antibody.

12. The method of claim 9, wherein the antibody is a full-length antibody.

13. The method of claim 9, wherein the antibody is humanized.

14. The method of claim 9, wherein the antibody is an antigen binding fragment of an antibody.

15. The method of claim 14, wherein the antigen binding fragment of the antibody is a Fv, Fab, Fab', scFv, diabody, or F(ab')2.

16. A method for capturing a polypeptide containing a modified IgG heavy chain constant region in a sample, wherein the method comprises contacting a sample containing a modified IgG heavy chain capable of being bound by the antibody of claim 1 with the antibody.

17. The method of claim 16, wherein capturing of the polypeptide by the antibody is determined by ELISA or surface plasmon resonance.

18. The method of claim 16, wherein the antibody is a monoclonal antibody.

19. The method of claim 16, wherein the antibody is a full-length antibody.

20. The method of claim 16, wherein the antibody is humanized.

21. The method of claim 16, wherein the antibody is an antigen binding fragment of an antibody.

22. The method of claim 21, wherein the antigen binding fragment of the antibody is a Fv, Fab, Fab', scFv, diabody, or F(ab')2.

23. A method for detecting a polypeptide containing a modified IgG heavy chain constant region in a sample, wherein the method comprises contacting a sample containing a modified IgG heavy chain capable of being bound by the antibody of claim 8 with the antibody.

24. The method of claim 23, wherein detection of the polypeptide by binding the antibody is determined by ELISA or surface plasmon resonance.

25. A method for capturing a polypeptide containing a modified IgG heavy chain constant region in a sample, wherein the method comprises contacting a sample containing a modified IgG heavy chain capable of being bound by the antibody of claim 8 with the antibody.

26. The method of claim 25, wherein capturing of the polypeptide by the antibody is determined by ELISA or surface plasmon resonance.

* * * * *

SEQUENCE LISTING

<160> NUMBER OF SEQ ID NOS: 10

<210> SEQ ID NO 1
<211> LENGTH: 114
<212> TYPE: PRT
<213> ORGANISM: Oryctolagus cuniculus

<400> SEQUENCE: 1

```
Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Asn Tyr Ala
            20                  25                  30

Val Gly Trp Val Arg Gln Ala Pro Gly Lys Gly Leu Glu Tyr Ile Gly
        35                  40                  45

Ile Ile Tyr Ala Ser Gly Ser Ala Tyr Tyr Ala Ser Trp Ala Lys Gly
    50                  55                  60

Arg Phe Thr Ile Ser Lys Thr Ser Thr Thr Val Asp Leu Lys Val
65                  70                  75                  80

Thr Ser Leu Thr Thr Glu Asp Thr Ala Thr Tyr Phe Cys Ala Arg Gly
            85                  90                  95

Tyr Gly Arg Ala Phe Arg Ile Trp Gly Pro Gly Thr Leu Val Thr Val
            100                 105                 110

Ser Ser
```

<210> SEQ ID NO 2
<211> LENGTH: 5
<212> TYPE: PRT
<213> ORGANISM: Oryctolagus cuniculus

<400> SEQUENCE: 2

```
Asn Tyr Ala Val Gly
1               5
```

<210> SEQ ID NO 3
<211> LENGTH: 16
<212> TYPE: PRT
<213> ORGANISM: Oryctolagus cuniculus

<400> SEQUENCE: 3

```
Ile Ile Tyr Ala Ser Gly Ser Ala Tyr Tyr Ala Ser Trp Ala Lys Gly
1               5                   10                  15
```

<210> SEQ ID NO 4
<211> LENGTH: 8
<212> TYPE: PRT
<213> ORGANISM: Oryctolagus cuniculus

```
<400> SEQUENCE: 4

Gly Tyr Gly Arg Ala Phe Arg Ile
1               5

<210> SEQ ID NO 5
<211> LENGTH: 109
<212> TYPE: PRT
<213> ORGANISM: Oryctolagus cuniculus

<400> SEQUENCE: 5

Ala Val Leu Thr Gln Thr Pro Ser Pro Val Ser Ala Ala Val Gly Gly
1               5                   10                  15

Thr Val Thr Ile Ser Cys Gln Ala Ser Gln Ser Val Tyr Asn Asn Asn
                20                  25                  30

Phe Leu Ser Trp Tyr Gln Gln Lys Pro Gly Gln Arg Pro Lys Leu Leu
            35                  40                  45

Ile Tyr Asp Ala Ser Thr Leu Glu Ser Gly Val Pro Ser Arg Phe Ser
    50                  55                  60

Gly Ser Gly Ser Gly Thr Gln Phe Thr Leu Thr Ile Ser Ser Val Gln
65                  70                  75                  80

Cys Asp Asp Ala Ala Thr Tyr Tyr Cys Leu Gly Gly Tyr Asp Asp His
                85                  90                  95

Asp Asn Ala Phe Gly Gly Gly Thr Glu Val Val Val Lys
            100                 105

<210> SEQ ID NO 6
<211> LENGTH: 13
<212> TYPE: PRT
<213> ORGANISM: Oryctolagus cuniculus

<400> SEQUENCE: 6

Gln Ala Ser Gln Ser Val Tyr Asn Asn Asn Phe Leu Ser
1               5                   10

<210> SEQ ID NO 7
<211> LENGTH: 7
<212> TYPE: PRT
<213> ORGANISM: Oryctolagus cuniculus

<400> SEQUENCE: 7

Asp Ala Ser Thr Leu Glu Ser
1               5

<210> SEQ ID NO 8
<211> LENGTH: 10
<212> TYPE: PRT
<213> ORGANISM: Oryctolagus cuniculus

<400> SEQUENCE: 8

Leu Gly Gly Tyr Asp Asp His Asp Asn Ala
1               5                   10

<210> SEQ ID NO 9
<211> LENGTH: 323
<212> TYPE: PRT
<213> ORGANISM: Oryctolagus cuniculus

<400> SEQUENCE: 9

Gly Gln Pro Lys Ala Pro Ser Val Phe Pro Leu Ala Pro Cys Cys Gly
1               5                   10                  15
```

-continued

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
            35                  40                  45

Gly Val Arg Thr Phe Pro Ser Val Arg Gln Ser Ser Gly Leu Tyr Ser
 50                  55                  60

Leu Ser Ser Val Val Ser Val Thr Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Met Cys Pro Pro Glu Leu Leu Gly
            100                 105                 110

Gly Pro Ser Val Phe Ile Phe Pro Pro Lys Pro Lys Asp Thr Leu Met
            115                 120                 125

Ile Ser Arg Thr Pro Glu Val Thr Cys Val Val Val Asp Val Ser Gln
        130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Thr
            260                 265                 270

Val Leu Asp Ser Asp Gly Ser Tyr Phe Leu Tyr Ser Lys Leu Ser Val
        275                 280                 285

Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 10
<211> LENGTH: 104
<212> TYPE: PRT
<213> ORGANISM: Oryctolagus cuniculus

<400> SEQUENCE: 10

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
            35                  40                  45

Thr Gly Ile Glu Asn Ser Lys Thr Pro Gln Asn Ser Ala Asp Cys Thr
        50                  55                  60

```
Tyr Asn Leu Ser Ser Thr Leu Thr Leu Thr Ser Thr Gln Tyr Asn Ser
65              70              75              80

His Lys Glu Tyr Thr Cys Lys Val Thr Gln Gly Thr Thr Ser Val Val
                85              90              95

Gln Ser Phe Asn Arg Gly Asp Cys
            100
```